United States Patent
Jin et al.

(10) Patent No.: US 10,883,984 B1
(45) Date of Patent: Jan. 5, 2021

(54) METHOD FOR PREPARING NANOCOMPOSITE AND LABEL-FREE APTAMER ELECTROCHEMICAL SENSOR OF GAMMA-INTERFERON BASED ON THE NANOCOMPOSITE

(71) Applicant: Qingdao University, Qingdao (CN)

(72) Inventors: Hui Jin, Qingdao (CN); Xiaohui Gao, Qingdao (CN); Rijun Gui, Qingdao (CN); Zonghua Wang, Qingdao (CN)

(73) Assignee: QINGDAO UNIVERSITY, Qingdao (CN)

( * ) Notice: Subject to any disclaimer, the term of this patent is extended or adjusted under 35 U.S.C. 154(b) by 0 days.

(21) Appl. No.: 16/627,344

(22) PCT Filed: Mar. 21, 2019

(86) PCT No.: PCT/CN2019/078997
§ 371 (c)(1),
(2) Date: Dec. 30, 2019

(87) PCT Pub. No.: WO2020/168607
PCT Pub. Date: Aug. 27, 2020

(30) Foreign Application Priority Data

Feb. 20, 2019 (CN) .......................... 2019 1 0125057

(51) Int. Cl.
*G01N 27/26* (2006.01)
*G01N 27/30* (2006.01)
*G01N 27/327* (2006.01)
*G01N 33/531* (2006.01)
*G01N 33/543* (2006.01)
*B82Y 15/00* (2011.01)
*B82Y 30/00* (2011.01)
*C12N 15/115* (2010.01)

(52) U.S. Cl.
CPC ....... *G01N 33/5438* (2013.01); *C12N 15/115* (2013.01); *C12N 2310/16* (2013.01); *C12N 2310/531* (2013.01); *G01N 2333/57* (2013.01)

(58) Field of Classification Search
CPC .......... G01N 33/5438; G01N 2333/57; C12N 15/115; C12N 2310/16; C12N 2310/531
See application file for complete search history.

(56) References Cited

U.S. PATENT DOCUMENTS

| 10,309,921 B2 * | 6/2019 | Bhansali | ............ | G01N 27/3272 |
| 2010/0099109 A1 | 4/2010 | Fantl et al. | | |

FOREIGN PATENT DOCUMENTS

| CN | 1766599 A | 5/2006 |
| CN | 101221185 A | 7/2008 |
| CN | 103472238 A | 12/2013 |
| CN | 103675076 A | 3/2014 |
| CN | 103940872 A | 7/2014 |
| CN | 104090116 A | 10/2014 |
| CN | 105806908 A | 7/2016 |
| CN | 105806909 A | 7/2016 |
| CN | 105973963 A | 9/2016 |
| CN | 106841351 A | 6/2017 |

OTHER PUBLICATIONS

Ying Liu et al., Detecting multiple cell-secreted cytokines from the same aptamer functionalized electrode, Biosensors and Bioelectronics, 2015, pp. 43-50, 64.

Khalil Abnous et al., A triple-helix molecular switch-based electrochemical aptasensor for interferon-gamma using a electrode and Methylene Blue as a redox probe, Microchim Acta, 2017, pp. 4151-4157, 184.

Jun-Tao Cao et al., Cathodic electrochemiluminescence behaviour of MoS2 quantum dots and its biosensing of microRNA-21, Analyst, 2018, pp. 3702-3707, 143.

Begard Kavosi et al., Ultrasensitive electrochemical immunosensor for PSA biomarker detection in prostate cancer cells using gold nanoparticles/PAMAM dendrimer loaded with enzyme linked aptamer as integrated triple signal amplification strategy, Biosensors and Bioelectronics, 2015, pp. 915-923.

* cited by examiner

*Primary Examiner* — David C Thomas
(74) *Attorney, Agent, or Firm* — Bayramoglu Law Offices LLC

(57) ABSTRACT

A method for preparing a label-free aptamer electrochemical sensor of γ-interferon based on a dendrimer/gold nanoparticle/molybdenum disulfide nanocomposite is provided. The nanocomposite is drip-coated on a surface of an electrode to prepare a modified electrode, and a terminal sulfhydryl group of a γ-interferon aptamer chain is connected to the gold nanoparticle via Au—S bond to obtain a nanocomposite-aptamer modified electrode. When γ-interferon is present, the γ-interferon specifically binds to the aptamer chain on the sensor, resulting in the aptamer's hairpin structure being opened and stretched, which can effectively adsorb methylene blue MB in the electrolyte, causing significant enhancement of MB redox signal. A linear relationship between a current intensity of MB oxidation peak and a concentration of the γ-interferon is fitted to construct the label-free aptamer electrochemical sensor of γ-interferon.

6 Claims, 2 Drawing Sheets

METHOD FOR PREPARING NANOCOMPOSITE AND LABEL-FREE APTAMER ELECTROCHEMICAL SENSOR OF GAMMA-INTERFERON BASED ON THE NANOCOMPOSITE

CROSS REFERENCE TO THE RELATED APPLICATIONS

This application is the national phase entry of International Application No. PCT/CN2019/078997, filed on Mar. 21, 2019, which is based upon and claims priority to Chinese Patent Application No. 201910125057.7, filed on Feb. 20, 2019, the entire contents of which are incorporated herein by reference.

TECHNICAL FIELD

The present disclosure belongs to the technical field of electrochemical biosensor and nanocomposite preparation, and more specifically relates to a method for preparing a dendrimer/gold nanoparticle/molybdenum disulfide nanocomposite and a label-free aptamer electrochemical sensor based on the nanocomposite. The sensor can be used for highly sensitive and selective detection of interferon gamma (γ-interferon).

BACKGROUND

γ-interferon is a cell-secreted cytokine that is the only member of the type II class of interferons, also known as a macrophage-activating factor. Aberrant γ-interferon expression is associated with a number of diseases, such as inflammatory bowel disease, genital herpes simplex virus infection, Alzheimer's disease, and others. Sensitive detection of γ-interferon may be used to study the activity of immune response and the diagnosis of infectious diseases. Qualitative or quantitative detection of γ-interferon by enzyme-linked immunosorbent assay can determine whether the human body is infected with *Mycobacterium tuberculosis*. Cytokines are usually detected by antibody immunoassays, however, these antibody immunoassays are time-consuming, require multiple washes, and require multiple-step processing to obtain the results. It is difficult to achieve the dynamic monitoring of cell secretions by the detection of antibodies due to complex washing and labeling. Additionally, the efficiency of the enzyme-catalyzed reaction may cause fluctuations of the output signal, resulting in an unsatisfactory reproducibility of the detection results and prolonged analysis time.

Nucleic acid aptamers are an effective substitute of antibodies, because of thermal and chemical stability, reproducibility, easy modification, and others. Currently, a series of aptamer sensors have been developed based on the technology of nucleic acid aptamer specific binding target molecules. These sensors are unique in that an oligonucleotide is designed as a signal mark, and when a target analyte binds to the oligonucleotide, a signal is generated without the need for the labeling and washing steps. The adaptive isomer biosensor's simple detection processes is particularly suitable for real-time and dynamic detection of biological samples, and may be broadly applied elsewhere.

For the nucleic acid aptamer electrochemical sensor, an aptamer is used as a molecular recognition element, which is fixed to a signal converter by a specific method, and then connected by electronic wires to form a device. Combined with electrochemical methods, the nucleic acid aptamer electrochemical sensor can be used for qualitative and quantitative detection of the object to be measured. Compared with traditional electrochemical analysis methods, electrochemical aptamer sensors have the advantages of high sensitivity, wide detection range, easy production, good selectivity, accuracy, and reproducibility in biomolecule detection. Researchers have developed a nucleic acid aptamer-based immunoglobulin detection strategy, where the γ-interferon aptamer labeled with a redox probe (methylene blue or ferrocene) is assembled on an electrode through a series of electrode surface modifications, and the changes of the electrochemical signal at the electrode are measured to quantify the concentration of γ-interferon. Liu et al. prepared an aptamer-functionalized electrode for the detection of cell-secreted cytokines, including γ- and α-interferon (Y. Liu, Y. Liu, Z. Matharu, A. Rahimian, A. Revzin, Detecting multiple cell-secreted cytokines from the same aptamer-functionalized electrode, *Biosensors and Bioelectronics* 2015, 64: 43-50). Abnous et al. developed a triple-helix molecular switch-based electrochemical aptasensor for the detection of γ-interferon using Methylene Blue as a redox probe (K. Abnous, N. M. Danesh, M. Ramezani, M. Alibolandi, K. Y. Hassanabad, A. S. Emrani, A. Bahreyni, S. M. Taghdisi, A triple-helix molecular switch-based electrochemical aptasensor for interferon-gamma using a gold electrode and Methylene Blue as a redox probe, *Microchimica Acta* 2017, 184: 4151-4157).

Patents related to sensors for detecting interferon have been reported. For example, Rui Zhao et al. disclosed methods for preparing a biosensor for detecting human β-interferon and a special polypeptide thereof, where the recognition element is a polypeptide containing a specific amino acid sequence or a derivative thereof (Rui Zhao, Jia Luo, Qundan Zhang, Guoquan Liu. Biosensor for detecting human β-interferon and special peptide thereof. Chinese Invention Patent. Publication No. CN101221185). Zhanjun Yang et al. developed an impedance immunosensor based on zinc oxide nanomaterials for label-free electrochemical immunoassay of bovine gamma interferon (Zhanjun Yang, Piya Qin, Xiang Chen. Preparation method of impedance immunosensor for bovine gamma interferon based on zinc oxide nanomaterials. Chinese Invention Patent. Publication No. CN104090116A). In recent years, label-free aptasensors research has attracted widespread attention. Compared with the traditional aptamer labeled sensor, the label-free aptasensor has certain advantages such as easy production, label-free aptamer and inexpensive. Based on this, in the present disclosure, a label-free aptamer electrochemical sensor based on a novel dendrimer/gold nanoparticle/molybdenum disulfide nanocomposite is designed for efficient γ-interferon detection. Thus far, there are no domestic and foreign literatures and patent reports on the dendrimer/gold nanoparticle/molybdenum disulfide nanocomposite, and the nanocomposite-based label-free aptamer electrochemical sensor.

SUMMARY

The objective of the present disclosure is to overcome the drawbacks of the prior art mentioned above, and to design a label-free aptamer electrochemical sensor based on a dendrimer/gold nanoparticle/molybdenum disulfide nanocomposite with the benefits of simple preparation, economical, high sensitivity, good selectivity, and others. The prepared sensor can be used for highly sensitive and selective detection of γ-interferon.

In order to achieve the above objective, the present disclosure relates to a preparation process of a label-free aptamer electrochemical sensor of γ-interferon based on a dendrimer/gold nanoparticle/molybdenum disulfide nanocomposite, including the steps as follows.

1. A method for preparing a nanocomposite and a label-free aptamer electrochemical sensor of γ-interferon based on the nanocomposite, characterized in that, the method specifically includes the following steps:

(1) adding molybdenum disulfide ($MoS_2$) powder to a mixed solvent of ethanol and distilled water, performing an ultrasonic treatment in a water bath, then centrifuging to separate, and removing the precipitate to obtain a $MoS_2$ homogeneous dispersion for subsequent use;

(2) preparing an aqueous solution of chloroauric acid and adding the aqueous solution of chloroauric acid to an aqueous solution of poly(amidoamine) dendrimer (PAMAM), stirring and mixing evenly with magnetic stirring, dropwise adding an aqueous solution of sodium borohydride to prepare gold nanoparticle-supported dendrimers (PAMAM/AuNPs), and removing residual reactants by dialysis treatment;

(3) dropwise adding the PAMAM/AuNPs dispersion to the $MoS_2$ homogeneous dispersion; performing an ultrasonic treatment in a water bath, and then performing a magnetic stirring treatment to carry out a reaction to obtain a PAMAM/AuNPs/$MoS_2$ nanocomposite;

(4) adding a cross-linking agent Nafion to a surface of a bare glass carbon electrode subjected to a polishing treatment, and then drip-coating the nanocomposite dispersion to obtain a PAMAM/AuNPs/$MoS_2$ modified electrode; diluting a γ-interferon nucleic acid aptamer with a buffer solution, heating to a certain temperature, and then cooling to room temperature, allowing the aptamer to form a secondary hairpin structure, and a sulfhydryl group at the terminal of the aptamer chain to be connected to a surface of AuNPs via Au—S bond; and (5) adding a redox probe methylene blue (MB) into an electrolyte immersed with the PAMAM/AuNPs/$MoS_2$-aptamer modified electrode; with an increasing of a target molecule γ-interferon, an electrochemical signal peak of the MB enhances gradually; then, fitting a linear relationship between a current intensity of MB oxidation peak and a concentration of the γ-interferon to construct a label-free aptamer electrochemical sensor for detecting the γ-interferon.

In step (1), an ultrasonic power is 150-200 W, a frequency is 20-50 kHz, an ultrasonic time is 5-10 h, and a concentration of the $MoS_2$ homogeneous dispersion is 1-2 mg mL$^{-1}$.

In step (2), the concentration of the chloroauric acid is 10-50 mM, the mass concentration of the PAMAM is 0.1-1%, the concentration of the sodium borohydride is 0.5-1 M, and the concentration of the PAMAM/AuNPs dispersion is 1-10 mg mL$^{-1}$.

In step (3), the time for the ultrasonic treatment is 10-60 minutes, the time for the magnetic stirring treatment is 6-12 hours, and the mass concentration ratio of the $MoS_2$ to the PAMAM/AuNPs ranges from (1:10) to (1:2).

In step (4), the concentration of the aptamer is diluted to 1-5 μM; the heating temperature is 50-100° C.; and the heating time is 1-6 hours.

In step (5), the concentration of the γ-interferon is 0-1000 pg mL$^{-1}$; and the detection limit of the γ-interferon is 1-3 fg mL$^{-1}$.

The advantages of the present invention are as follows. The PAMAM/AuNPs/$MoS_2$ composite is drip-coated on the surface of a bare glass carbon electrode to prepare a modified electrode, and the thiol terminal of the γ-interferon aptamer chain is connected to the surface of AuNPs via Au—S bond to prepare a PAMAM/AuNPs/$MoS_2$-aptamer modified electrode. $MoS_2$ is selected as a substrate for electrochemical reactions, and AuNPs grown on the PAMAM are used as binding sites for the label-free aptamer chains, and then a label-free electrochemical aptamer sensor based on the nanocomposite is constructed. When γ-interferon is present, the γ-interferon specifically binds to the aptamer chain on the sensor, resulting in the destruction of the aptamer's hairpin structure and the aptamer chain being opened and stretched, which can effectively adsorb the MB in the electrolyte, causing significant enhancement of MB redox signal. The linear relationship between the current intensity of the MB oxidation peak and the concentration of the γ-interferon is fitted to construct a label-free aptamer electrochemical sensor for detecting the γ-interferon. Compared with the prior art, the method of the present disclosure has the advantages of easy operation, low cost, high sensitivity and good selectivity, and may be developed into a novel label-free aptamer electrochemical sensor for highly sensitive and selective detection of γ-interferon in biological samples.

DETAILED DESCRIPTION OF THE EMBODIMENTS

The present invention is described in detail below with reference to the drawings and specific embodiments.

Embodiment 1

Figure 1:
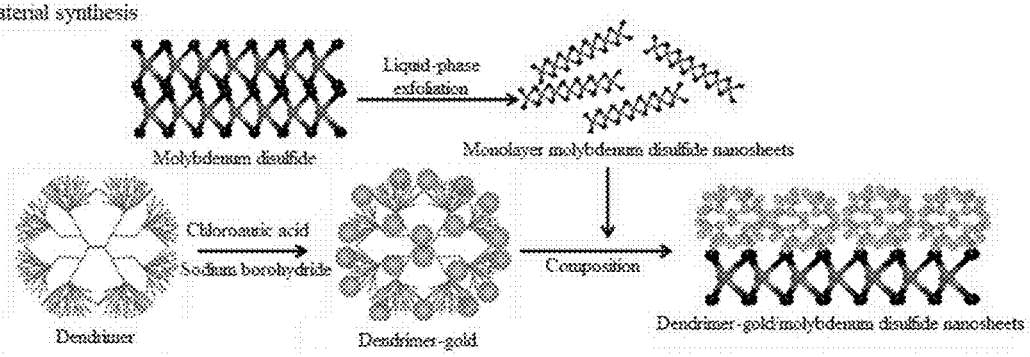
FIG. 1 is a schematic diagram showing a preparation process of a dendrimer/gold nanoparticle/molybdenum disulfide nanocomposite, a label-free aptamer electrochemical sensor based on the nanocomposite, and a principle of γ-interferon detection according to the present invention.
Figure 1:
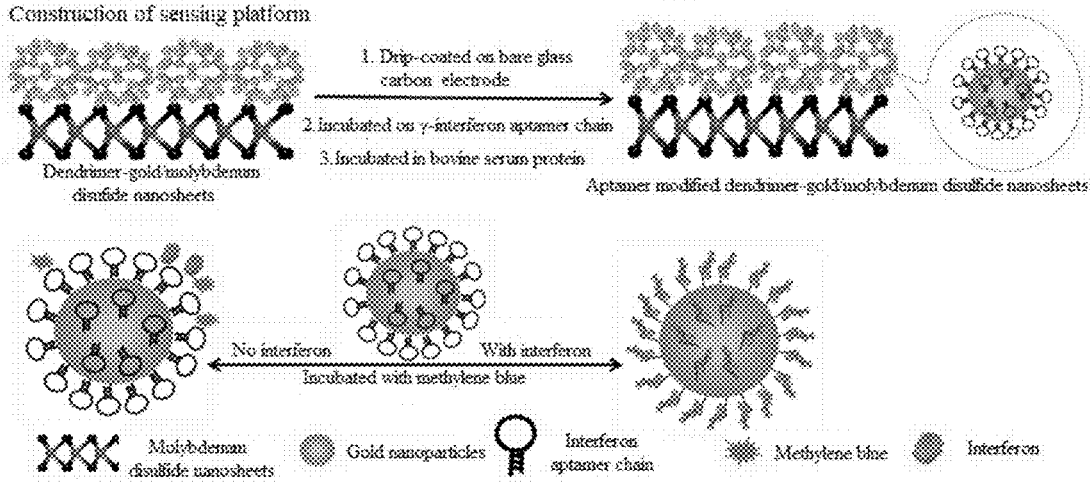

The present invention relates to a preparation of a dendrimer/gold nanoparticle/molybdenum disulfide nanocomposite and a label-free aptamer electrochemical sensor based on the nanocomposite and an electrochemical detection of γ-interferon. The schematic diagram of the preparation process and principle are shown in FIG. 1. The specific process steps are as follows.

30 mg of $MoS_2$ powder was added to a mixed solvent of ethanol/distilled water (with a ratio of 1:1 by volume), subjected to an ultrasonic treatment in a water bath for 8 h (180 W, 40 kHz), then centrifugated at 3000 rpm for 20 min, and a precipitate was removed to obtain a $MoS_2$ homogeneous dispersion (1.5 mg mL$^{-1}$) for subsequent use. 25 mM aqueous solution of chloroauric acid was prepared, 10 mL of the aqueous solution of chloroauric acid was added to an aqueous solution of poly(amidoamine) dendrimer (PAMAM, 1 wt %, 15 mL), magnetic stirring was performed for 1 hour for evenly mixing, and then an aqueous solution of sodium borohydride (0.5 M) was added dropwise until the solution changed from pale yellow to reddish-brown. The products were subjected to dialysis to remove residual reactants, and gold nanoparticle-supported dendrimers (PAMAM/AuNPs, 1 mg mL$^{-1}$) were obtained for subsequent use. The PAMAM/AuNPs dispersion was added dropwise to the MoS$_2$ dispersion with a mass ratio of 1:2. An ultrasonic treatment in a water bath was performed for 30 min, and then a magnetic stirring treatment was performed for 12 hours to carry out a reaction to obtain a PAMAM/AuNPs/MoS$_2$ nanocomposite.

Figure 2A:
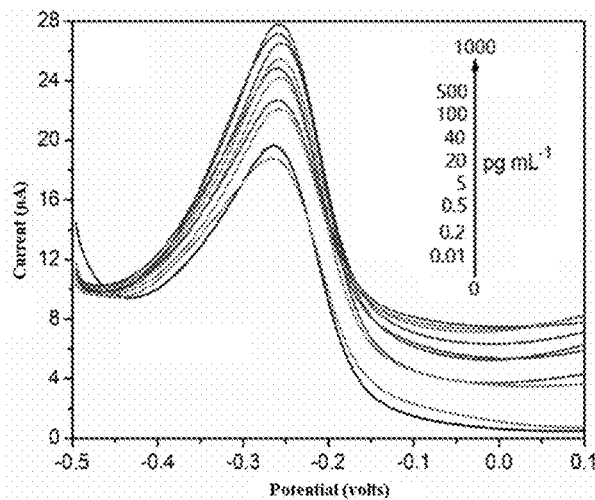
FIG. 2A is an electrochemical square wave voltammetry curve corresponding to different concentrations of γ-interferon by a label-free aptamer electrochemical sensor of the present invention.
Figure 2B:
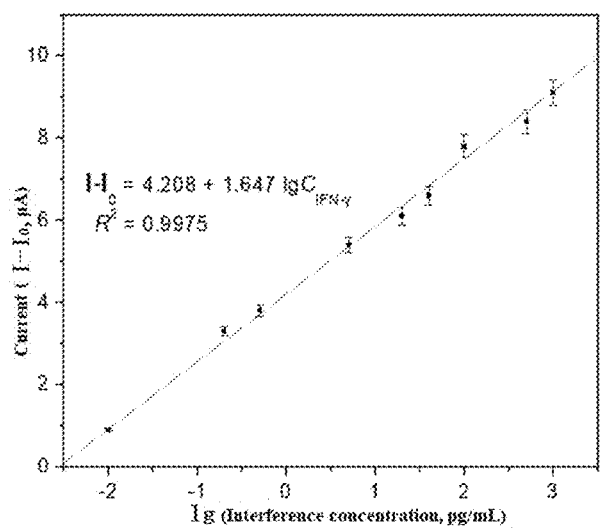
FIG. 2B is a diagram showing a fitted linear relationship between different intensities of oxidative current peaks and concentrations of γ-interferon, corresponding to oxidation current peak intensities of methylene blue, in the presence of different concentrations of γ-interferon.

A cross-linking agent Nafion was added dropwise on a surface of a bare glass carbon electrode subjected to a polishing treatment, and a nanocomposite dispersion was drip-coated on the surface of the bare glass carbon electrode to obtain a PAMAM/AuNPs/MoS$_2$ modified electrode. A γ-interferon nucleic acid aptamer was diluted to 5 μM with a buffer solution, followed by heating to 90° C. and maintaining for 5 hours, and then cooled to room temperature. The aptamer formed a secondary hairpin structure, and the sulfhydryl group at the terminal of the aptamer chain was connected to the surface of AuNPs via Au—S bond. In an electrolyte immersed with the PAMAM/AuNPs/MoS$_2$-aptamer modified electrode, 10 mM Tris-HCl buffer was contained, and a redox probe methylene blue MB (1 mM) was added. With an increasing of the target molecule γ-interferon, an electrochemical signal peak of the MB enhanced gradually. Then, a linear relationship between a current intensity of MB oxidation peak and a concentration of the γ-interferon was fitted to construct a label-free aptamer electrochemical sensor for detecting the γ-interferon. As shown in FIGS. 2A-2B, the linear detection range of γ-interferon concentration is 0.01-1000 ng mL$^{-1}$, and the detection limit is 3 fg mL$^{-1}$.

Embodiment 2

In this embodiment, a preparation of a dendrimer/gold nanoparticle/molybdenum disulfide nanocomposite and a label-free aptamer electrochemical sensor based on the nanocomposite, and an electrochemical detection of γ-interferon are provided. The schematic diagram of the preparation process and principle are the same as that in Embodiment 1. The specific process steps are as follows.

30 mg of MoS$_2$ powder was added to a mixed solvent of ethanol/distilled water (with a ratio of 1:1 by volume), subjected to an ultrasonic treatment in a water bath for 6 hours (150 W, 30 kHz), then centrifugated at 3000 rpm for 20 min, and a precipitate was removed to prepare a MoS$_2$ homogeneous dispersion (1 mg mL$^{-1}$) for subsequent use. 15 mM aqueous solution of chloroauric acid was prepared, 10 mL of the aqueous solution of chloroauric acid was added to an aqueous solution of poly (amidoamine) dendrime (PAMAM, 0.5 wt %, 15 mL), magnetic stirring was performed for 1 hour for evenly mixing, and then an aqueous solution of sodium borohydride (0.5 M) was added dropwise until the solution changed from pale yellow to reddish-brown. The products were subjected to dialysis to remove residual reactants, and gold nanoparticle-supported dendrimers (PAMAM/AuNPs, 2 mg mL$^{-1}$) were obtained for subsequent use. The PAMAM/AuNPs dispersion was added dropwise to the MoS$_2$ dispersion with a mass ratio of 1:4. An ultrasonic treatment in a water bath was performed for 20 min, and then a magnetic stirring treatment was performed for 6 hours to carry out a reaction to obtain a PAMAM/AuNPs/MoS$_2$ nanocomposite.

A cross-linking agent Nafion was added dropwise on a surface of a bare glass carbon electrode subjected to a polishing treatment, and a nanocomposite dispersion was drip-coated on the surface of the bare glass carbon electrode to obtain a PAMAM/AuNPs/MoS$_2$ modified electrode. A γ-interferon nucleic acid aptamer was diluted to 2 μM with a buffer solution, followed by heating to 80° C. and maintaining for 3 hours, and then cooled to room temperature. The aptamer formed a secondary hairpin structure, and the sulfhydryl group at the terminal of the aptamer chain was connected to the surface of AuNPs via Au—S bond. In an electrolyte immersed with the PAMAM/AuNPs/MoS$_2$-aptamer modified electrode, 10 mM Tris-HCl buffer was contained, and a redox probe methylene blue MB (1 mM) was added. With an increasing of the target molecule γ-interferon, an electrochemical signal peak of the MB enhanced gradually. Then, a linear relationship between a current intensity of MB oxidation peak and a concentration of the γ-interferon was fitted to construct a label-free aptamer electrochemical sensor for detecting the γ-interferon. As shown in FIGS. 2A-2B, the linear detection range of γ-interferon concentration is 0.01-500 ng mL$^{-1}$, and the detection limit is 2.5 fg mL$^{-1}$.

Embodiment 3

In this embodiment, a preparation of a dendrimer/gold nanoparticle/molybdenum disulfide nanocomposite and a label-free aptamer electrochemical sensor based on the nanocomposite, and an electrochemical detection of γ-interferon are provided. The schematic diagram of the preparation process and principle are the same as that in Embodiment 1. The specific process steps are as follows.

30 mg of MoS$_2$ powder was added to a mixed solvent of ethanol/distilled water (with a ratio of 1:1 by volume), subjected to an ultrasonic treatment in a water bath for 10 hours (200 W, 50 kHz), then centrifugated at 3000 rpm for 20 min, and a precipitate was removed to obtain a MoS$_2$ homogeneous dispersion (2 mg mL$^{-1}$) for subsequent use. 50 mM aqueous solution of chloroauric acid was prepared, 10 mL of the aqueous solution of chloroauric acid was added to an aqueous solution of poly(amidoamine) dendrimer (PAMAM, 1 wt %, 15 mL), magnetic stirring was performed for 1 hour for evenly mixing, and then an aqueous solution of sodium borohydride (1 M) was added dropwise until the solution changed from pale yellow to reddish-brown. The products were subjected to dialysis to remove residual reactants, and gold nanoparticle-supported dendrimers (PAMAM/AuNPs, 10 mg mL$^{-1}$) were obtained for subsequent use. The PAMAM/AuNPs dispersion was added dropwise to the MoS$_2$ dispersion with a mass ratio of 1:5. An ultrasonic treatment in a water bath was performed for 60 min, and then a magnetic stirring treatment was performed for 12 hours to carry out a reaction to obtain a PAMAM/AuNPs/MoS$_2$ nanocomposite.

A cross-linking agent Nafion was added dropwise on a surface of a bare glass carbon electrode subjected to a polishing treatment, and a nanocomposite dispersion was drip-coated on the surface of the bare glass carbon electrode to obtain a PAMAM/AuNPs/MoS$_2$ modified electrode. A γ-interferon nucleic acid aptamer was diluted to 5 μM with a buffer solution, followed by heating to 90° C. and maintaining for 6 hours, and then cooled to room temperature. The aptamer formed a secondary hairpin structure, and the sulfhydryl group at the terminal of the aptamer chain was connected to the surface of AuNPs via Au—S bond. In an electrolyte immersed with the PAMAM/AuNPs/MoS$_2$- aptamer modified electrode, 10 mM Tris-HCl buffer was contained, and a redox probe methylene blue MB (1 mM) was added. With an increasing of a target molecule γ-interferon, an electrochemical signal peak of the MB enhanced gradually. Then, a linear relationship between a current intensity of MB oxidation peak and a concentration of the γ-interferon was fitted to construct a label-free aptamer electrochemical sensor for detecting the γ-interferon. As shown in FIGS. 2A-2B, the linear detection range of γ-interferon concentration is 0.01-800 ng mL$^{-1}$, and the detection limit is 2 fg mL$^{-1}$.

The foregoing descriptions are preferred embodiments of the present invention. It should be noted that numerous improvements and modifications may be made by those of ordinary skill in the art without departing from the principles of the present disclosure, and such improvements and modifications shall also be considered to be within the protection scope of the present disclosure.

What is claimed is:

1. A method for preparing a nanocomposite and a label-free aptamer electrochemical sensor of γ-interferon based on the nanocomposite, comprising the following steps:
    (1) adding molybdenum disulfide (MoS$_2$) powder to a mixed solvent of ethanol and distilled water to obtain a first mixed solution, performing a first ultrasonic treatment on the first mixed solution in a water bath, then centrifuging the first mixed solution to separate and remove a precipitate to obtain a MoS$_2$ homogeneous dispersion for subsequent use;
    (2) preparing an aqueous solution of chloroauric acid and adding the aqueous solution of chloroauric acid to an aqueous solution of poly(amidoamine) dendrimer (PAMAM) to obtain a second mixed solution, stirring and mixing the second mixed solution evenly with magnetic stirring, dropwise adding an aqueous solution of sodium borohydride to the second mixed solution to obtain a gold nanoparticles (AuNPs)-supported dendrimers (PAMAM/AuNPs) dispersion, and removing residual reactants from the PAMAM/AuNPs dispersion by a dialysis treatment;
    (3) dropwise adding the PAMAM/AuNPs dispersion to the MoS$_2$ homogeneous dispersion to obtain a third mixed solution; performing a second ultrasonic treatment on the third mixed solution in a water bath and then performing a magnetic stirring treatment to the third mixed solution to carry out a reaction to obtain a PAMAM/AuNPs/MoS$_2$ nanocomposite dispersion;
    (4) adding a cross-linking agent to a surface of a bare glass carbon electrode subjected to a polishing treatment, and then drip-coating the PAMAM/AuNPs/MoS$_2$ nanocomposite dispersion to obtain a PAMAM/AuNPs/MoS$_2$ modified electrode; diluting a γ-interferon nucleic acid aptamer with a buffer solution to obtain a fourth mixed solution, heating the fourth mixed solution to a predetermined temperature, and then cooling the fourth mixed solution to room temperature, allowing the fourth mixed solution to form an aptamer chain with a secondary hairpin structure, and thus allowing a sulfhydryl group at a terminal of the aptamer chain to be connected to a surface of the AuNPs via an Au—S bond to obtain a PAMAM/AuNPs/MoS$_2$-aptamer modified electrode; and
    (5) adding a redox probe methylene blue (MB) into an electrolyte immersed with the PAMAM/AuNPs/MoS$_2$-aptamer modified electrode; wherein, with an increasing of γ-interferon, an electrochemical signal peak of the MB enhances gradually; then, fitting a linear relationship between a current intensity of the electrochemical signal peak of the MB and a concentration of the γ-interferon to construct the label-free aptamer electrochemical sensor for detecting the γ-interferon.

2. The method for preparing the nanocomposite and the label-free aptamer electrochemical sensor of the γ-interferon based on the nanocomposite according to claim 1, wherein, in the first ultrasonic treatment of the step (1), an ultrasonic power is 150-200 W, a frequency is 20-50 kHz, an ultrasonic time is 5-10 hours, and a concentration of the MoS$_2$ homogeneous dispersion is 1-2 mg mL$^{-1}$.

3. The method for preparing the nanocomposite and the label-free aptamer electrochemical sensor of the γ-interferon based on the nanocomposite according to claim 1, wherein, in the step (2), a concentration of the aqueous solution of chloroauric acid is 10-50 mM, a mass concentration of the aqueous solution of PAMAM is 0.1-1%, a concentration of the aqueous solution of sodium borohydride is 0.5-1 M, and a concentration of the PAMAM/AuNPs dispersion is 1-10 mg mL$^{-1}$.

4. The method for preparing the nanocomposite and the label-free aptamer electrochemical sensor of the γ-interferon based on the nanocomposite according to claim 1, wherein, in the step (3), the second ultrasonic treatment is performed for 10-60 minutes, the magnetic stirring treatment is performed for 6-12 hours, and a mass concentration ratio of the MoS$_2$ homogeneous dispersion to the PAMAM/AuNPs dispersion ranges from (1:10) to (1:2).

5. The method for preparing the nanocomposite and the label-free aptamer electrochemical sensor of the γ-interferon based on the nanocomposite according to claim 1, wherein, in the step (4), the γ-interferon nucleic acid aptamer is diluted to a concentration of 1-5 μM; the predetermined temperature is 50-100° C.; and a heating time is 1-6 hours.

6. The method for preparing the nanocomposite and the label-free aptamer electrochemical sensor of the γ-interferon based on the nanocomposite according to claim 1, wherein, in the step (5), a concentration of the γ-interferon is 0-1000 pg mL$^{-1}$; and a detection limit of the γ-interferon is 1-3 fg mL$^{-1}$.

* * * * *